US006791687B1

(12) United States Patent
Rushbrooke et al.

(10) Patent No.: US 6,791,687 B1
(45) Date of Patent: Sep. 14, 2004

(54) IMAGING SYSTEM FOR LUMINESCENCE ASSAYS

(75) Inventors: John Gordon Rushbrooke, Cambridge (GB); Claire Elizabeth Hooper, Cambridge (GB)

(73) Assignee: Packard Instrument Company, Inc., Meriden, CT (US)

(*) Notice: Subject to any disclaimer, the term of this patent is extended or adjusted under 35 U.S.C. 154(b) by 0 days.

(21) Appl. No.: 09/720,118

(22) PCT Filed: Jul. 20, 1999

(86) PCT No.: PCT/GB99/02344

§ 371 (c)(1),
(2), (4) Date: Feb. 27, 2001

(87) PCT Pub. No.: WO00/05568

PCT Pub. Date: Feb. 3, 2000

(30) Foreign Application Priority Data

Jul. 21, 1998 (GB) .............................................. 9815701

(51) Int. Cl.[7] .............................................. G01N 21/25
(52) U.S. Cl. ........................ 356/417; 356/416; 356/317
(58) Field of Search ................................ 356/417, 416, 356/317, 318; 250/458.1, 459.1, 461.1, 461.2; 422/82.05, 82.06, 82.07, 82.08, 52; 436/172

(56) References Cited

U.S. PATENT DOCUMENTS

| | | | |
|---|---|---|---|
| 4,113,384 A | | 9/1978 | Lauer et al. ................... 356/70 |
| 4,622,469 A | * | 11/1986 | Akiyama .................. 250/458.1 |
| 5,424,841 A | * | 6/1995 | Van Gelder et al. ...... 250/458.1 |
| 5,426,306 A | * | 6/1995 | Kolber et al. ............ 250/458.1 |
| 5,615,673 A | | 4/1997 | Berger et al. ............... 128/633 |
| 5,697,373 A | | 12/1997 | Richards-Kortum et al. ............. 128/664 |
| 5,698,397 A | * | 12/1997 | Zarling et al. ................. 216/25 |
| 5,736,410 A | | 4/1998 | Zarling et al. .............. 436/172 |
| 6,556,299 B1 | * | 4/2003 | Rushbrooke et al. ....... 356/417 |

FOREIGN PATENT DOCUMENTS

| GB | 2 315 130 A | 1/1998 |
|---|---|---|
| JP | 07270718 | 10/1995 |

OTHER PUBLICATIONS

PCT International Application WO 98/01743, J. G. Rushbrooke, C. E. Hooper, W. W. Wray, 'Improvements in and relating to imaging', PCT/GB97/018525, Published Jan. 15, 1998, Filed Jul. 4, 1997.*
Preston, "Micellar electrokinetic capillary chromatography with laser–induced fluorimetric detection of amines in beer", Journal of Chromatography B, vol. 695, No. 1, Jul.18, 1997, pp. 175–180.

* cited by examiner

*Primary Examiner*—Thong Nguyen
*Assistant Examiner*—Arnel C. Lavarias
(74) *Attorney, Agent, or Firm*—Barnes & Thornburg LLP

(57) ABSTRACT

Apparatus for detecting light emitted by an assay sample is provided, in which light emitted by the sample is collected for transmission to a photosensitive detector such as a charge coupled device (CCD) (74) by an optical fiber 78 bundle. The cross-sectional area of the optical fiber bundle corresponds to the area of the sample, the end of which is located close to the sample for detecting any light emitted therefrom. Selected fibers (30) of those making up the bundle may be separated from the remainder and extend to a source of excitation radiation (76) to convey excitation radiation to the sample. The remaining fibers (32, 38) serve to collect emitted light and provide a light path to the photosensitive detector (74). A blocking filter and an interference filter are placed between the fiber bundle and the detector. The blocking filter may be between the bundle and the interference filter or between the latter and the detector. Two blocking filters may be provided one ahead of and the other downstream from the interference filter. The attenuation characteristic of the two filters may be different or the same.

16 Claims, 2 Drawing Sheets

96 holes
spacing-3.9mm
in circle-75mm diam.

192 holes diam-2.0mm
spacing-1.9mm
within 27 x 27mm
area of camera

IMAGING SYSTEM FOR LUMINESCENCE ASSAYS

FIELD OF INVENTION

This invention concerns methods and apparatus or imaging and particularly the imaging of light emitting luminescence samples of the type in which the sample is illuminated with excitation radiation such as ultra-violet light, or where the sample is activated by some suitable chemiluminescent or bioluminescent means and is interrogated for any resulting emission light due for example to fluorescence within the sample. The invention is particularly concerned with multipath (or multichannel) systems fin which a large number of samples can emit light and need to be interrogated at the same time.

BACKGROUND TO THE INVENTION

PCT Application WO 98/01744 describes an imaging system for fluorescence assays in which an interference filter is used to enable highly selective transmission of the radiation which is to reach the imaging device such as a camera.

Whilst an interference filter has a very sharp cut-off and allows virtually 100% transmission of desired wavelengths and virtually zero transmission of unwanted wavelengths, breakthrough can occur it light of a non acceptable wavelength is incident on the filter at a sufficiently large angle to satisfy the Fabry-Perot transmission criterion for the interference filter, ie the relationship between wavelength and angle of incidence for the interference filter. The unwanted wavelengths may be attributable to light emitted by the sample however it is stimulated.

By using optical fibres to transmit light from the sample to the interference filter, and shielding the fibre ends from extraneous light as much as possible, rogue rays will in general be restricted to reflected or refracted light, which may be excitation light, or light emitted by the sample due to activation by chemiluminescent or bioluminescent means, and this will in general be of a fixed wavelength. Rays of such light which are capable of being transmitted via the optical fibres and are of such large angle as to be capable of breaking through the interference filter would probably be Skew rays and it has already been proposed in the aforementioned PCT Application to position an angle collimator between the interference filter and the camera to reduce the transfer to the camera of Skew rays issuing from the interference filter.

It is an object of the present invention to further improve the blocking of such Skew rays and thereby further reduce the incidence of unwanted radiation on the detector.

In the fluorescence assay imaging system described in PCT Application No. WO 98/01744, excitation radiation is supplied to the assay sample via an annular sleeve fitted around the end of a fibre optic bundle the end of which is in close proximity to the assay sample. The fibres collect emitted light due to fluorescence induced by the excitation radiation. It has been found that using an annular source of radiation does not produce the most uniform and sufficiently intense illumination of the assay reaction site, and it is a further object of the present invention to improve the uniformity and intensity of excitation illumination over the presented area of each assay reaction site, without prejudicing any light collecting efficiency of the fibres.

Achieving uniformity over the reaction site has been found to be even more difficult to achieve where the sample is a very thin layer of cells or is contained or upon a thin gel or membrane.

The problem identified above become even greater as the area of each reaction site decreases. This is tending to occur as greater numbers of samples and therefore reaction sites, are accommodated in a sample supporting device such as a multi-well plate, multi-side membrane or gel or wafer, or chip of silicon or like material.

It is therefore a further object of the invention to provide an improved illumination and collection system which allows sufficient excitation radiation, if required by the assay, to be introduced to, and emitted light to be collected from, reaction sites such as those in a 96 well plate (for which the earlier imaging system of WO 98/01744 is generally adequate) as well as the much smaller reaction sites such as now exist in high format multiple sample plates containing many hundreds or even a few thousand reaction sites per plate.

The invention is applicable to any luminescence producing assay.

Light emitting luminescence processes, including fluorescence, chemiluminescence and bioluminescence, and/or a combination of these processes, can be used in the measurements of biomedical and chemical assays. The wavelengths of excitation and emission for these processes are characteristic of the fluorescent and/or luminescent molecules and moieties being used. Wavelength ranges used are in the UV, visible, red and infra-red parts of the spectrum. A typical excitation range is 260–800 nm, a typical emission range is 320–1100 nm.

In the present Application, the luminescent processes being measured include fluorescence, chemi- and bioluminescence.

In normal fluorescence, a fluorescent molecule or fluorophore is excited by external radiation, such that it absorbs light energy and re-emits light at a longer wavelength. The fluorescence may occur almost immediately, or later in time in which event it is referred to as time-delayed fluorescence.

In an alternative luminescent process, involving what is generally known as fluorescence or chemiluminescence energy transfer, energy is transferred from a donor molecule or moiety to an acceptor molecule or moiety, via a non-radiative mechanism. This mechanism can occur, eg via resonance or via electron transfer between atoms and molecules. Such luminescent donor and acceptor molecules may be fluorescent or chemi- or bioluminescent. The donor or acceptor molecules are generally different, and more than one molecule type may be used in either the donor or acceptor stage of the process.

The activation of the donor molecules may be via excitation light in the case of fluorescence or via chemical activation in the case of chemi- or bioluminescence. With fluorescence activation there may be a short delay between the excitation of the donor and the emission of the acceptor, in the range microseconds to milliseconds.

Energy transfer only takes place over very short distances (typically 100 nm) and therefore the donor and acceptor molecules need so be in very close proximity. This can be achieved by direct bonding (eg covalent) of the donor and acceptor molecules, or linking of the two molecules by a biochemical bridge (eg via a peptide link). Alternatively, the molecules may be coated or bonded onto a solid phase, such that they are in close proximity (eg a microplate or bead). In a further example, the energy transfer from the donor may be via a reactive intermediate product, eg singlet oxygen or some excited chemical radical, which diffuses, eg in a fluid, to interact with the acceptor molecule.

Where no energy transfer takes place between the donor and the acceptor molecules, the donor molecule itself, when activated, will release energy directly as light, with emission wavelength characteristic of that molecule itself. When energy transfer occurs, the emission wavelength is characteristic of the acceptor molecule. Where the donor and acceptor molecules are different, the light emission from the acceptor molecules may be of a longer or shorter wavelength to the emission characteristic of the donor molecule.

When used in biomedical or chemical assays, to measure the presence or activity of a compound or agent, these luminescent processes may be used as an indicator of the presence or activity of such a compound or agent. The increase or decrease in light emission, from the donor or acceptor molecules, may be used as an indicator of the unknown compound being assayed. For example, the unknown compound might interact directly or indirectly with the energy transfer process, eg break the bridge between the donor and acceptor molecules or otherwise inhibit the transfer process. This would result in a change in the relative intensity of light emission of the donor and acceptor molecules, which could be detected by measurement, for example, at the two or more wavelengths which are characteristic of each molecule. Thus a radiometric measurement involving various pairs or wavelengths characteristic of the molecules used may be appropriate.

EP 0580362 A1 describes a fluorescence detecting apparatus in which some of the fibres terminating below a sealed sample holder 7 convey excitation radiation to the sample, and others convey the fluorescence radiation away to a detector. On pages 3 and 4, a preferred arrangement for weak fluorescence is described, in which the excitation fibres are concentrated in the centre of the bundle presented to the sample and those for receiving and conveying away from the fluorescence radiation are located annularly around the central excitation fibre core.

It was no doubt thought that by concentrating the excitation radiation fibres into a central region of the sample, and collating the weak emitted fluorescence from an annular region of the central core, much of the unwanted excitation radiation reflected or refracted back towards the fibres by the sample (or the reaction site), would thereby not be collected by the fibres leading to the detector.

However it has been found that this creates a virtual dead region in the centre of the reaction site where the product of excitation and light collection for any point is very low or zero (due to the annular arrangement of the collecting fibres), and genuine signals cannot be distinguished from background noise emanating from a large central area of the reaction site.

The improved light collection system proposed by the present invention also seeks to overcome this problem since for reliable and accurate assay evaluation, not only is it necessary for good uniformity of response to exist between one well and another over the entire well plate, but it is also very important that there is a high degree of uniformity of response across the area of each assay reaction site.

U.S. Pat. No. 4,113,384 discloses a sample fluorescence detector system wherein, before the fluorescence rays are incident on a detector, they pass through an interference filter and windows which serve as blocking filters for higher order passbands of the interference filter. In contrast, the present invention is not concerned with rays meeting higher order passband conditions of the interference filter, which rays can be transmitted through the interference filter at all angles, including 0 degrees, but with skew rays, as heretofore explained.

SUMMARY OF THE INVENTION

According to one aspect of the present invention there is provided apparatus for detecting induced luminescence in an assay sample, in which light emitted by the sample is collected for transmission to photosensitive detector means by a bundle of optical fibres and in which at least one interference filter selecting the wavelength $\lambda$em is located between the optical fibre bundle and the detector, and wherein a blocking filter is positioned between the bundle and the detector, the attenuation characteristics of the blocking filter being such as to block rays of wavelength $\lambda$ex <$\lambda$em, which if incident on the interference filter as skew rays can satisfy the Fabry-Perot transmission condition for the interference filter and thereby break through the interference filter to the detector.

Where the blocking filter is located in advance of a interference filter, between it and the ends of optical fibres transmitting light from the sample, skew rays will be strongly attenuated before reaching the interference filter irrespective of the angle of incidence of the radiation on the blocking filter.

Where the blocking filter is located after an interference filter, between it and the detector, skew rays which have broken through the interference filter will be attenuated before they reach the detector.

Where two or more different interference filters are employed, each being selective of a different wavelength, and optical fibres leading from the assay are divided equally between the two or more interference filters, either a separate blocking filter is provided between the ends of the optical fibres and each separate interference filter, or one large blocking filter is provided encompassing all the interference filters, and the divided bundles of optical fibres terminate at the face of the large filter, at locations opposite each of the interference filters, or separate filters are provided beyond the interference filters in registry with the fibre optic bundles conveying the emitted light to the different interference filters, or a large filter which encompasses all the interference filters is located beyond the latter in advance of the detector.

Positioning a blocking filter ahead of the interference filter can remove light rays such as arise from excitation radiation or other unwanted light emitted by a sample, and emitted from the fibres as skew rays, that can be transmitted through the interference filter, and can have a sufficient intensity at the detector as compared with the intensity of wanted radiation due to assay luminescence, as to swamp, or be confused with, the latter, at the detector.

A first blocking filter may be located between the bundle and the interference filter and a second blocking filter may be located between the interference filter and the detector. The attenuation wavelength of the first filter may be different from that of the second, or may be the same.

Where a blocking filter is located between the interference filter and the detector, it may also be selected to reduce the transmission of unwanted fluorescence emitted by the interference filter. Preferably, of course the materials forming the interference and blocking filter or filters, are selected for their low fluorescence properties.

The characteristics of the emission filters required for detection of these types of luminescent processes, especially where the emission wavelengths of the acceptor molecules may be shorter or longer than the wavelengths of the donor molecule, has to be considered.

In the case of fluorescein, which produces normal fluorescence, excitation light of, eg 485 nm, produces fluorescent light emitted at a longer wavelength, eg 530 nm.

Any excitation light appearing at a 530 nm band pass interference filter, with an angle to the filter satisfying the Fabry-Perot condition, will be transmitted. This is the case, eg for 485 nm light arriving at ~54°. In the case of fibre optic components, skew rays can be transmitted and enter the filter at such an angle. A blocking filter is needed to eliminate any light which might be transmitted by virtue of the Fabry-Perot condition, or by punch-through.

In the case of fluorescence energy transfer assays, where the excitation light is used to activate the donor molecules, and is say of wavelength 480 nm, and is of shorter wavelength than the light emitted by the acceptor molecule, eg 540 nm, then the same situation applies. This means that a blocking filter is required to absorb the 480 nm excitation light that would otherwise be transmitted by the Fabry-Perot condition for the interference filter which is chosen to transmit the 540 nm emission light. The blocking filter also helps to eliminate any punch-through of the 480 nm light.

In the case of energy transfer assays where chemi- or bioluminescent activation of the donor molecules occurs, and hence no excitation light is used, there is still the problem arising from the donor or acceptor molecules having different emission wavelengths, and hence the need to detect the longer wavelength in the presence of the shorter wavelength, where the intensity of the shorter wavelength is significantly greater than the intensity of the longer wavelength.

This is particularly the case where the emission wavelength of the acceptor is shorter than the emission wavelength of the donor, and where the energy transfer process has resulted in significant amplification of the signal generated by the acceptor molecules. Again a blocking filter is desirable to prevent light of shorter wavelength being passed by the interference filter, which will normally only transmit longer wavelength light, by virtue of the shorter wavelength light being transmitted through the filter by satisfying the Fabry-Perot condition, or by punch-through.

In a typical example, blue excitation light having a wavelength of 485 nm is employed to excite green fluorescence having a wavelength of the order of 530 nm. Any blue light finding its way down fibres which should only transmit emitted green fluorescence, for example by reflection from the bottom of a sample plate containing the assay, may exit the fibres in a cone of Skew rays of sufficiently large angle to satisfy the Fabry-Perot transmission condition of the interference filter, and an intense ring of blue light will be presented to the detector.

Without the presence of the blocking filter proposed by the invention, this unwanted light will be conveyed via the remaining fibre optics to the detector (camera). Unless this ring of blue light is eliminated by an angle collimating device ahead of the camera as already proposed, the ring of light will swamp the detector in the very region of the detector to which low level green light due to sample fluorescence, will be conveyed, if present.

Although an angle collimator will reduce the intensity of such a ring, it is not a complete solution to the problem, and in the presence of strong Skew rays, sufficient swamping can still occur to render green light at the detector virtually indistinguishable from noise etc. If the assay emits light for example by fluorescence, the small spot of green light attributable to the fluorescence can be surrounded by and essentially swamped by the ring of intense blue light produced by the unwanted breakthrough of excitation radiation even in the presence of an angle collimator. A blocking filter, as proposed by the invention, fitted ahead of, or downstream of or both ahead and downstream of the interference filter, reduces this significantly.

To be effective the blocking filter should have a sharp cut-off between transmission and attenuation, and a high attenuation of wavelengths-beyond the cut-off point. In the example given above where the blue light wavelength is 485 nm and the emitted radiation due eg to fluorescence has a wavelength of 530 nm, a filter having a cut-off at 515 nm has been found to be appropriate, thereby transmitting (albeit with some attenuation) wavelengths of the order of 530 nm, but very significantly inhibiting wavelengths of the order of 485 nm.

A filter having such a characteristic is a Schott filter, Type OG515. This transmits wavelengths of 515 nm with a 50% transmission factor and above 515 nm with an increasingly greater transmission factor, but severely attenuates wavelengths below 515 nm, and at 485 nm is highly attenuating.

The use of a blocking filter provided by the invention does not obviate the need for an angle collimator as already proposed, but is preferably used in combination therewith.

The angle collimating device further reduces Skew rays and in practice is comprised of a fused fibre optic plate of the order of 5–10 mm thickness, which is mounted in advance of the detector/camera input. Preferably it is made from glass fibres of relatively low numerical aperture (NA) typically of the order of 0.30. Such a device transmits wanted rays within the numerical aperture 0.22 of the bundle of fibres, but greatly reduces Skew rays that would otherwise be transmitted by the bundle.

By inserting the plate immediately in front of the detector/camera input face plate, any tendency for spreading or cross-talk between the fibres and the detecto-/camera input is reduced.

If the angle collimating device is placed after the interference filter it is less important if the material from which the collimating device is constructed itself produces any fluorescence. It is for example difficult to obtain a fused fibre optic plate of non-fluorescent material such as silica.

Reference has been made to Skew rays. In this connection the numerical aperture of a fibre is the cone-angle for the rays that are transferred with high efficiency by the fibre. In an ideal sense the condition only applies to meridional rays, ie those which pass along a plane including the axis of the fibre. The fibre is normally assumed to be a long cylinder.

In practice such rays are vanishingly few and the light transmitted by a fibre is normally considered to be all the rays within the same cone angle but entering the fibre at any point on the entry face of the fibre, since all these rays will also be transmitted with relatively high efficiency.

Skew rays are therefore those that enter at any point on the end face of the fibre but at an angle greater than $\sin^{-1}$ NA. The conditions for such rays to be transmitted are complicated and difficult to satisfy but in some situations up to half the rays transmitted by a fibre can be Skew rays.

In single channel assay systems, Skew rays are less of a problem since the light path in a single channel system can be highly collimated so as to more effectively remove them. The problem is more noticeable in multichannel systems, where there is insufficient space between the channels to allow optical collimating mechanisms to be accommodated for individually collimating each of the channels.

The photosensitive detector is preferably a CCD, an ICCD, a cooled CCD, a photodiode array, or an array of PMT's. Whatever device is chosen, it should have good spatial resolution after centroiding so as to be able to resolve individual fibre bundles in the final image to give minimal cross-talk between channels. A preferred spatial resolution is 10–20 microns.

The detector should have good quantum efficiency (QE).

Typically an ICCD will have a QE of 15% in the blue, falling to a few percent in the red.

A cooled CCD will have better QE rising to approximately 30% in the red.

When the optical system presenting light to the detector/camera collects light from the sample via 100 micron diameter fibres (typically of the order of 100 microns diameter or less), and maintains this resolution throughout to the input of the photodetector, such as a CCD camera, and where the latter has a spatial resolution of the order of 10–20 microns, inspection of the area of the CCD array on which any light from one sample is incident, will allow light from individual fibres in the bundles conveying light from the sample to the camera to be identified. This for example enables light from a clump of cells in a sample to be observed, as distinct and different from light from separated individual cells, which can be useful.

Where this requires a focusing of the light passing through the interference filter region, a GRIN lens or other device may be used, such as is described in our aforementioned PCT Application WO 98/01744.

It is to be understood that the provision of one or more blocking filters in accordance with the present invention can be incorporated in all such systems, including those incorporating different detectors, and those incorporating sub-well imaging using Grin lenses.

The blocking filter or filters may be formed from a material which absorbs unwanted wavelengths but transmits at wavelengths near to those of the light emitted by the assay, and of interest.

The invention also lies in a method of reducing unwanted wavelengths of light from reaching a photosensitive detector onto which light of a specific wavelength produced by a particular occurrence in an assay sample will fall in the presence of the said occurrence, comprising the steps of: gathering the light from the sample by a fibre optic bundle, filtering all light leaving the bundle for the detector by means of two filters in series, one being an interference filter and the other a blocking filter, and selecting the latter so as to significantly attenuate light having wavelengths which could be emitted by the fibre optic bundle as skew rays and which if incident in the interference filter can satisfy the Fabry-Perot transmission criterion for the interference filter and thereby break through the interference filter to the detector.

According to a further feature of the present invention, an apparatus for detecting luminnescene in an assay sample in which light emitted by the sample is collected for transmission to photosensitive detector means by an optical fibre bundle the cross-sectional area of which corresponds to the area of the sample and one end of which is located close to the sample for detecting any light emitted therefrom, selected ones of the fibres making up the bundle are seperated from the remainder and extend to a source of exitation radiation, and serve to convey excitation radiation (if required to produce fluorescence) directly to the sample, and the remainder of the bundle of fibres serve to collect emitted light whether due to fluorescence initiated by the excitation radiation or otherwise,and provide a light path to the photosensitive detector, wherein the ends of the excitation fibres and the ends of the light collecting fibres are distributed uniformly over the area of the fibre bundle presented to the sample.

The light collecting fibres forming the said remainder may be divided into two equal groups and convey light to two different regions on the detector, thereby providing two parallel light paths from the sample to the detector, and wavelength selective filters, conveniently interference filters, having Skew ray blocking means, are located in the two light oaths which only permit selected wavelengths of emitted light to reach the different regions of the detector if present in the light emitted from the sample.

Preferably the fibres making up each of the two equal groups are uniformly distributed across the area of the end of the bundle presented to the sample.

Preferably the ends of the said selected fibres which convey excitation radiation to the sample holder are also uniformly distributed over the whole of the area of the end of the bundle, presented to the sample holder.

In the preferred arrangement one third of the fibres in the bundle convey excitation radiation to the sample holder, another third of the fibres convey emitted radiation via a first wavelength selective filter to a specific region of the photosensitive detector, and the remaining third of the fibres convey emitted radiation via a second wavelength selective filter to another specific region of the detector.

Where the cross-sectional shape of the sample is generally circular and the fibre bundle is likewise generally circular in cross-section, the fibres are preferably arranged in a symmetrical pattern so that in the end face of the bundle presented to the sample holder each excitation fibre end is surrounded by a ring of six emission receiving fibre ends which, around the ring, alternately lead to the two different wavelength selected filters.

Except for peripheral regions of the fibre bundle area, each emission receiving fibre will be a member of each of three separate but intersecting rings of emission receiving fibres, centered on three excitation fibre ends which are immediate neighbours of one another.

By distributing the excitation fibres uniformly over the area presented to the sample, and likewise distributing the emission detecting fibres in a similar uniform manner, there is a greater chance that excitation radiation will penetrate to sites which are capable of luminescing, as by fluorescing, and there is also a good chance that the very small quantities of light emitted in response to such excitation will be collected by one of the emission detecting fibres, and conveyed to the photosensitive detector.

Typically the samples are contained in small wells arranged in a matrix in a plate known as a well plate, at least one end of each of the wells being closed so as to retain a liquid sample therein, but the closure is sufficiently thin and transparent as to enable excitation radiation to penetrate into the sample and not to impede light emitted due, for example to fluorescence, from the sample in the return direction through the base.

Assay analysis often involves studying reactions which have occurred in hundreds or thousands of samples and it is commonplace for well plates to be constructed having a matrix of some many hundreds or thousands of wells. One typical well plate contains 3456 wells which is conveniently interrogated by investigating the luminescence from 96 wells at a time, using a presentation plate which aligns 96 fibre bundles with 96 of the 3456 wells in the well plate, and stepping the presentation plate 36 times relative to the well plate so as to interrogate all 3456 wells.

In the case of a 3456 well plate having circular wells, typically each well has a diameter of 1 mm whereas in the case of a well plate having a smaller number of wells, each well can be larger. The wells can in fact be of any cross-sectional shape but normally are circular or square.

According to a preferred feature of the invention the two groups of emission gathering fibres from each of the 96 bundles are collated into two groups of 96 bundles, and each of the two groups are presented to an interference filter arrangement, each of which has a different filtering characteristic from the other, and further bundles of optical fibres transfer light capable of passing through each of the interference filters, to two discrete regions Oil the input faceplate of the detector.

Where the filters are circular, the groups of fibres from the presentation plate are preferably re-arranged so as to optimally utilise the area of the filter, and where the input faceplate to the detector has a non-circular aspect ratio the fibres leading from the filters to the input faceplate are preferably rearranged so as to optimally occupy the active area of the detector. Thus in the case of a detector having a square input faceplate window, the fibres leading from the interference filter are preferably arranged in two rectangular arrays making up a square corresponding in size to the square input window of the faceplate.

Although rearrangement of the fibre bundles occurs, by maintaining fixed registration between the 192 fibre bundle ends presented to the detector with the 192 fibre bundles derived from the 96 well inspecting bundles, the presence of emitted light from any one well can be determined by interrogating the X,Y coordinate positions in the detector array corresponding to the images of two fibre bundles in the two groups of 96 bundles presented to the detector, which correlate to the two groups of fibres from the fibre bundle inspecting the particular well.

According to a preferred aspect of the invention, each of the fibre optic bundles presented to each well site, is made up of 45 Ge-doped-silica clad, silica fibres, each typically of a diameter of 100–200 microns, 15 of which are separated out as a sub-bundle and combined with similar sub-bundles from each of the other 96 bundles, and which extend to a source of excitation radiation such as UV light. One or more filters may be located between the UV source and the sub-bundles. The remaining 30 fibres from each of the 96 bundles are divided into two further sub-bundles each of 15 fibres. This produces a total of 192 emission collecting sub-bundles, 96 of which lead to discreet positions at the input of a first interference filter, and the other 96 of which lead to discreet positions at the input of a second interference filter, which transmits different wavelengths from those transmitted by the first filter.

Light transmitted to the interference filters, enters one or the other of two downstream groups of 96 sub-bundles arranged on a one to one basis with each of the two arrangements of 96 sub-bundles upstream of the filters, and the downstream sub-bundles are merged to form an array of 192 sub-bundles having the same aspect ratio as that of the detector.

Where the aspect ratio of the detector is approximately square, the 192 sub-bundles are conveniently arranged into 14 rows, the first and last of which contain 12 sub-bundles and with each of the intermediate 12 rows, containing 14 sub-bundles. The array of rows and columns thereby defines what is essentially a square area with each of the corners missing, for presentation to a generally square aspect ratio detector.

Typically the interference filters are circular and have a diameter of approximately 80 mm.

It is also to be understood that whereas the various aspects of the invention have so far been described in relation to well plates, each of the aspects of the invention is equally applicable to assay systems in which the samples occupy discrete areas of a membrane or gel or are distributed in the matrix of a sample support such as a wafer or chip of silicone or thin glass slide or sheet.

BRIEF DESCRIPTION OF THE DRAWINGS

The invention will now be further described by way of example with reference to the accompanying drawings, in which.

DETAILED DESCRIPTION OF THE INVENTION

Figure 1A:
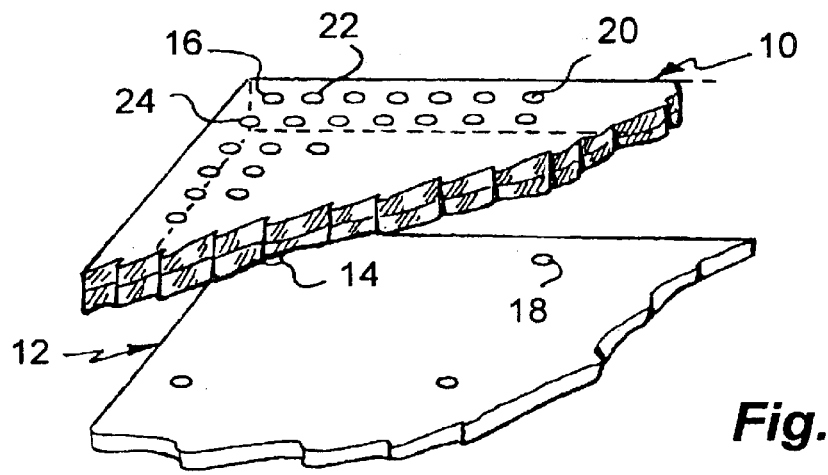
FIGS. 1 and 1A illustrate a wellplate located above a presentation plate.

Well plates have tended to be constructed with either 96 wells typically arranged in 8 rows of 12 columns, but in recent years higher density plates have been constructed and a typical high density plate may contain, say, 36 times as many wells as the 96 well plate. However the area of the plate is the same as is the basic matrix. The only difference in this case is that the well size has been decreased enabling six wells to be located along each row and six wells down each column in place of a single well in the original array. This means that instead of there being twelve wells along each row, there are now 72 and instead of there being eight rows, there are now 48 rows.

To take advantage of this and to simplify the indexing of a 96 aperture presentation plate, the latter is formed with openings which correspond in position to each of the original 96 wells of a 96 well plate, but equal in size to that of the wells in the 3456 well plate. This means that 96 of the 3456 wells can be inspected simultaneously by aligning the presentation plate 12 so that the first of the 96 apertures (14) coincides with the first of the 3456 wells, at position 16 in the well plate. This means that the second aperture 18 in the presentation plate aligns with the seventh well 20 along the first row, and so on.

Shifting the presentation plate 12 by a distance equal to the distance between wells 16 and 22 (the next well in the first row adjacent 16) means that all of the 96 apertures in the presentation plate 12 will now be aligned with a new set of 96 of the wells in the well plate 10. By moving the presentation plate successively through six steps parallel to the rows containing wells 16, 22 and 20, and for each step six positions perpendicular to that row, in each case each movement corresponding to the distance between adjoining wells in the well plate measured perpendicular to the first row, (ie the distance between well 16 and well 24), so every one of the 3456 wells can be interrogated by 36 relative movements between the presentation plate and the well plate.

In practice, the well plate is moved relative to the presentation plate.

Each of the apertures such as 14 in the presentation plate 12 serves as a termination for a fibre bundle made up of 45 individual fibres. The fibres are shown terminating in two of the apertures for illustration only, one designated 26 and the other 28.

Each bundle of 45 fibres is made up of three groups of 15, one group such as 30 extending to an excitation light source, one group such as 32 conveying fluorescence light from a well aligned with the aperture 26 to an aperture 34 in a presentation disc 36. The third group of 15 fibres 38 extends to another opening 40 in a second presentation disc 42, for conveying fluorescence light to that other opening 40.

The three groups of 15 fibres making up the other illustrated bundle leading to and from aperture 28 are denoted by reference numerals 44, 46 and 48 respectively and these extend from the excitation light source in the case of group 44 and to two other apertures 50 and 52 respectively in the two presentation discs 36 and 42.

Each of the latter includes 96 apertures arranged regularly over the circular area of each disc, and similar discs 36' and 42' are aligned with the discs 36 and 42. Suitable optical filter discs 54 and 56 are sandwiched between discs 36 and 36' and discs 42 and 42'.

Apertures in the two discs 36, 36' (42, 42') are aligned on a one to one basis and fibres lead from each of the aligned apertures such as 34' in disc 36' to unique apertures in two groups of 96 apertures arranged in a rectilinear matrix in an output plate generally designated 58. The first such matrix is designated 60 and the second 62 and the fibres such as 64 and 66 from aperture 34' and 50' lead to apertures 34" and 50" in the matrix region 60 and the fibres 68 and 70 from apertures 40' and 52' in disc 42' lead to apertures such as 40" and 52" in matrix 62.

The two matrixes 60 and 62 together form a generally square outline which conforms approximately to the square aspect ratio of an input window illustrated at 72 in a camera 74.

Figure 2:
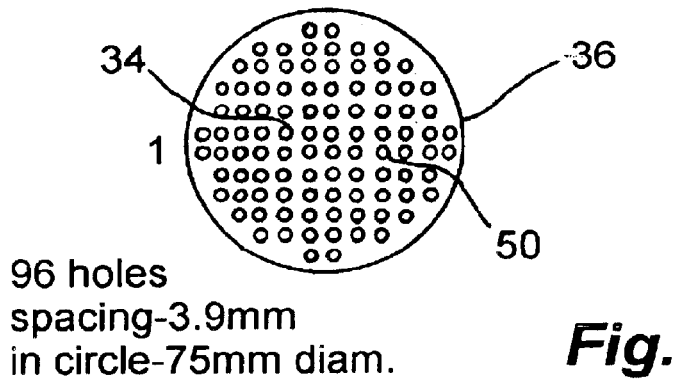
FIG. 2 is a plan view of a presentation disc.

The excitation light source is denoted by reference numeral 76 and between it and the 96 groups of 15 fibres such as 30 and 44 is located a filter 78. The arrangement of the apertures such as 34 and 50 and 40 and 52 on each of the plates 36 and 42 is as shown in FIG. 2. Two of the openings are arbitrarily shown at 34 and 36.

Figure 3:
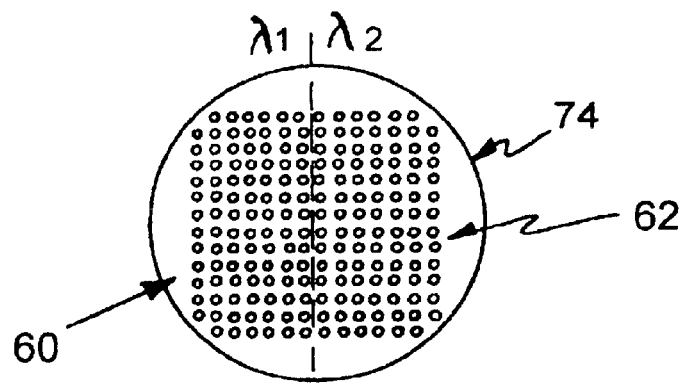
FIG. 3 illustrates arrangement of fibre ends in two matrices.

The arrangement of the two groups of 96 fibre ends in the two matrices 60 and 62 is shown in FIG. 3. The camera typically has a generally square aspect ratio and the arrangement of the 192 apertures making up the two matrices 60 and 62 makes the best use of the available generally square outline.

Figure 4:
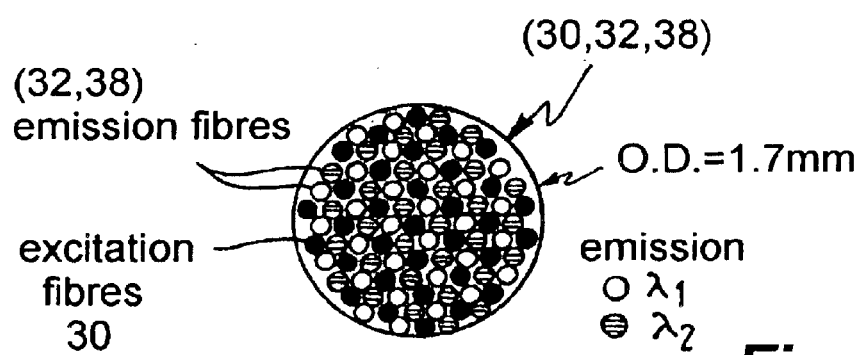
FIG. 4 shows three groups of fibres making up the bundle of fibres at each presentation plate aperture.

In accordance with a particularly preferred feature of the invention, the three groups of 15 fibres making up the bundle of fibres at each presentation plate aperture such as 16, is as shown in FIG. 4. Here the solid black fibre ends correspond to those in the excitation bundle 30, the clear circles correspond to those in the fibre bundle 32 leading to the first filter oath containing filter 54, and the shaded circle corresponds to the fibres in the bundle 38 leading to the other wavelength selective path containing the second filter 56.

Each of the fibres illustrated in FIG. 4 is typically of the order of 100–200 microns diameter and is a Germanium doped silica clad silica fibre having a numerical aperture of approximately 0.22. The fibre preferably includes a polyimide coating.

Using fibres of this size means that when bundled into a generally circular cross-section array the outside diameter of the bundle will be approximately 1.7 mm.

The particular arrangement of fibres shown in FIG. 4 has been found to be of considerable merit for ensuring high intensity of illumination from excitation light by ensuring that excitation fibre ends are uniformly distributed over the whole of the circular area of the fibre bundle and by uniformly arranging fibres leading to the two different wavelength selective paths equally uniformly throughout the remaining space, so an optimal excitation/collection characteristic is obtained for each well.

Although bundles of very tiny fibres are required between the presentation plate 12 and each of the presentation discs 36 and 42, the fibres leading from the discs 36' and 52' to the output plate 58 do not need to be made up of bundles of fibres but can be single fibres. Thus 64 for example may be a bundle of tiny fibres or a single fibre in each case having a typical outside diameter of 2 mm.

An angle collimating device 76 in the form of a thin plate may be located between the matrix array of fibre ends 34", 50" etc and the input window 72 of the camera 74.

The filters 54 and 56 are typically interference filters and preferably are interchangeable to allow different wavelengths to be selected.

Although the examples shown in the drawings are of a well plate, it is to be understood that the samples may be contained in any other supporting device such as a multi-well plate, multi-site membrane or gel or wafer or chip of silicon or like material.

Figure 1:
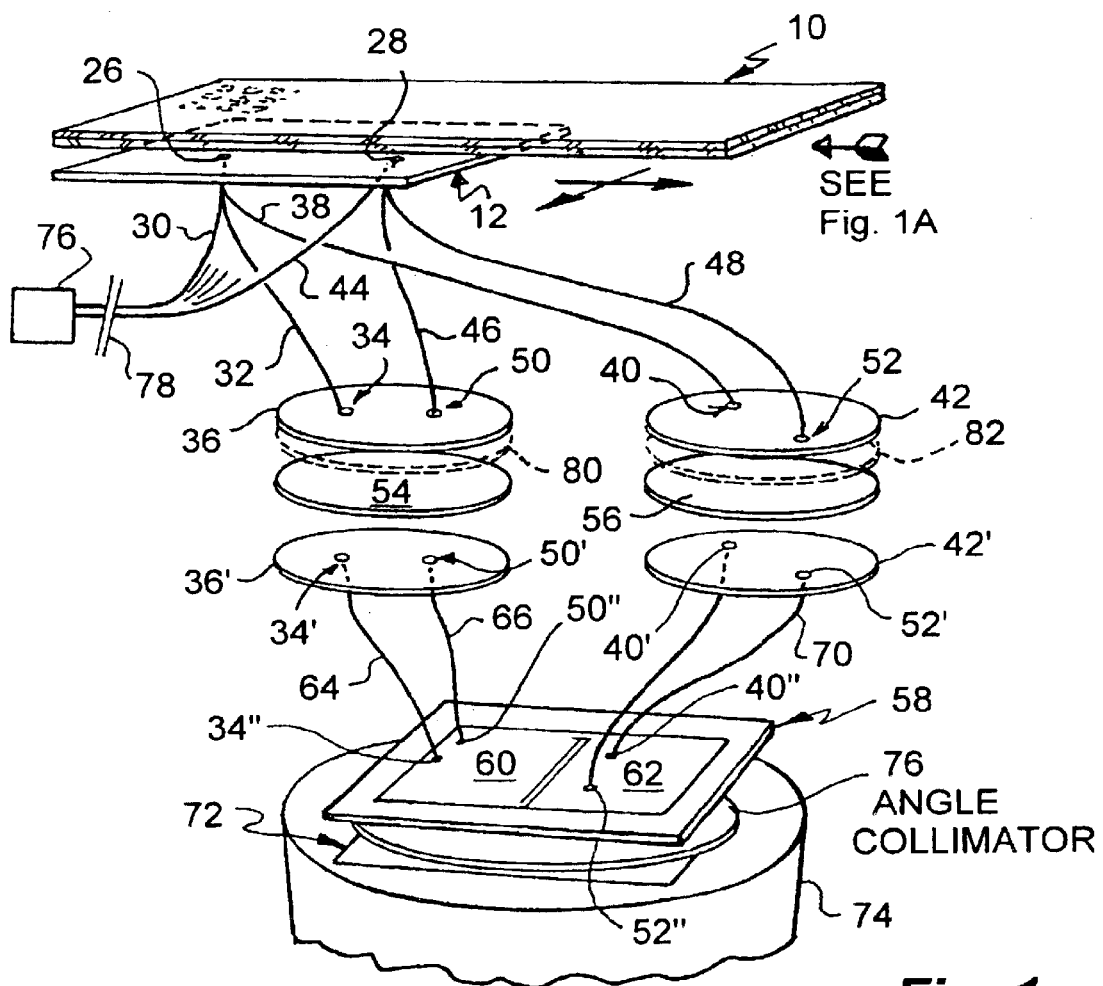

As indicated in FIG. 1 the area of presentation plate can be significantly less than the area of the well plate where there is a high ratio of samples to inspection apertures in the presentation plate. Also, provided the arrangement and spacing and number of inspection apertures is suitable to align with groups of samples, and the one can be stepped relative to the other to obtain differing registrations, the aspect ratio and size of the sample support and the presentation plate can be quite different.

In accordance with the invention filters 80, 82 for blocking Skew rays are incorporated, as shown in dashed line in FIG. 1, for the purpose hereinbefore described.

It is assumed that the interference filter is constituted from material which will not fluoresce, or any fluorescence produced by the filter is attenuated within the filter.

If the interference filter does produce sufficient unwanted fluorescence as to create a problem at the detector, then a second blocking filter may be required between the interference filter and the detector.

Interference Filters

As referred to herein, interference filters may comprise a large number of thin layers of dielectric materials, having differing refractive indices to produce constructive and destructive interference in transmitted light. Such filters can be designed to transmit a specific waveband only (a band pass filter) and can also be made to provide a very steep slope cut-on or cut-off at a particular wavelength, and to produce an edge filter.

Metallic layers may also be incorporated in such devices and in auxiliary blocking structures. Broadband interference filters usually contain a metallic layer.

Narrowband bandpass interference filters can be considered to be a Fabry-Perot interferometer, operating in the first order.

Examples of Blocking and Interference Filter Combinations

Example 1

Fluorescein—a Green Fluorescence Assay.

The peak excitation wavelength for Fluorescein in 485 nm and the peak of the emission is in the range 518–523 nm.

An interference filter is chosen whose peak transmission waveband is 525–530 nm and in accordance with the invention blocking filter is selected which attenuates wavelengths below 515 nm—such as a Schott OG 515 filter.

Example 2

Coumarin—a Blue Fluorescence Assay.

The peak excitation wavelength for Coumarin is 400 nm and the emission wavelength peaks in the range 455–460 nm.

An interference filter is chosen whose peak transmission wavelength is 460 nm and in accordance with the invention a blocking filter is selected which attenuates wavelengths below 455 nm—such as a Schott BG 455.

Example 3

Cy5—a Red Fluorescence Assay.

The peak excitation wavelength for Cy5 is 649 nm and the peak emission occurs at 670 nm.

An interference filter is chosen whose peak transmission wavelength is 680 nm and in accordance with the invention a blocking filter is selected which attenuates wavelengths below 665 nm—such as a Schott RG 665.

Example of Energy Transfer Assay

Here no excitation radiation is required to stimulate emission.

One example of a Donor moiety is Luciferase which is a bioluminescent enzyme. An acceptor moiety could be a green fluorescent protein such as is derived from Renilla.

In this case the Donor emission wavelength is 480 nm and the Acceptor emission wavelength is 520 nm.

If an interference filter is employed having a peak transmission wavelength of 530 nm, then the blocking filter is preferably one having a cut-off wavelength of 515nm—such as a Schott OG 515.

Where energy transfer occurs between donor and acceptor, the emission light to be measured is the acceptor emission at 520 nm.

When energy transfer does not take place, then there will be little or no emission from the acceptor but the donor will lose energy as light at its characteristic emission wavelength, of 480 nm in the above example.

In practice, both 520 nm and 480 nm will be monitored separately and the relative proportions the wavelengths are measured.

Since the energy transfer process is not 100% efficient, the donor constituent will continue to emit light at its characteristic wavelength of 430 nm and the acceptor emissions will have to be measured against a background of donor emission. Thus in the above example, 520 nm wavelength emissions will have to be measured against a background of donor emissions at 480 nm.

Successful filtering will usually be achieved by selecting a blocking filter having a sharp cut-off between transmission and attenuation and a high attenuation of wavelengths beyond the cut-off point, and the latter (at which 50% attenuation occurs) is closer in terms of luminescence than to the peak wavelength of the nearest component of any unwanted radiation.

Examples of energy transfer assays, such as bioluminescence and chemiluminescence assays are to be found in "Chemiluminescence: Principles and Applications in Biology and Medicine" by A. K. Campbell. 1988. Published by Ellis Harwood Ltd of Chichester, England.

What is claimed is:

1. Apparatus for detecting induced luminescence in an assay sample, in which light emitted by the sample is collected for transmission to photosensitive detector means by a bundle of optical fibres and in which at least one interference filter selecting a wavelength $\lambda em$ comprising the wavelength which is desired to reach the photosensitive detector, is located between the optical fibre bundle and the detector, and wherein an absorption filter is positioned between the bundle and the detector, the attenuation characteristics of the absorptions filter being such as to block rays of wavelength $\lambda ex<\lambda em$, where $\lambda ex$ comprises the wavelength of excitation radiation, which when incident on the interference filter as skew rays can satisfy the Fabry-Perot transmission condition for the interference filter and thereby break through the interference filter to the detector.

2. Apparatus according to claim 1, wherein the absorption filter is located in advance of the interference filter between it and the ends of the optical fibres transmitting light from the assay sample, so that the skew rays will be strongly attenuated before reaching the interference filter.

3. Apparatus according to claim 1, wherein a plurality of interference filters, each being selective of a different wavelength, are placed between the photosensitive detector means and the optical fibre bundle and an absorption filter is provided for each interference filter.

4. Apparatus according to claim 1, wherein a plurality of interference filters each being selective of a different wavelength, are placed between the photosensitive detector means and the optical fibre bundle and a single large area absorption filter is provided for all the interference filters.

5. Apparatus according to claim 1, wherein the absorption filter has a sharp cut-off between transmission and attenuation, and a high attenuation of wavelengths below the cut-off point and is selected to provide 50% attenuation at a wavelength closer to the wavelength of the induced luminescence than to the wavelength of the nearest component of the unwanted skew rays.

6. Apparatus according to claim 5, wherein the induced fluorescence is produced by fluorescein and the absorption filter is a Schott filter, Type OG515.

7. Apparatus according to claim 1, further comprising an angle collimating device.

8. Apparatus as claimed in claim 7 wherein the angle collimating device is a fused fibre optic plate.

9. Apparatus according to claim 7, wherein the angle collimating device is made from glass fibres of low numerical aperture of the order of 0.30.

10. Apparatus according to claim 1, wherein the photosensitive detector means has a charge coupled device, a cooled charge coupled device, or an intensified charge coupled device, or an array of photodiodes, or a PMT array.

11. Apparatus according to claim 10, wherein the photosensitive detector means has a spatial resolution of 10–20 microns.

12. Apparatus according to claim 1, further comprising a GRIN lens adapted to focus light passing through the wavelength selective interference filter.

13. Apparatus according to claim 1 in which the absorption filter is located between the inferference filter and the detector.

14. Apparatus according to claim 2, in which a second absorption filter is located between the interference filter and the detector.

15. Apparatus according to claim 14 wherein the second absorption filter attenuates light having a wavelength which is different from that which is attenuated by the absorption filter between the bundle and the interference filter.

16. A method of reducing unwanted wavelengths of light from reaching a photosensitive detector onto which light of a specific wavelength produced by a particular occurrence in an assay sample will fall in the presence of the said occurrence, comprising the steps of: gathering the light from the sample by a fibre optic bundle, filtering all light leaving the bundle for the detector by means of two filters in series, one being an interference filter and the other an absorption filter, and selecting the latter so as significantly attenuate light having wavelengths which could be emitted by the fibre optic bundle as skew rays and when incident on the interference filter can satisfy the Fabry-Perot transmission criterion for the interference filter and thereby break-therethrough the interference filter to the detector.

* * * * *